(12) United States Patent
Perkins et al.

(10) Patent No.: US 11,826,226 B2
(45) Date of Patent: Nov. 28, 2023

(54) MODULAR MULTIBRANCH STENT ASSEMBLY AND METHOD

(71) Applicant: Medtronic Vascular, Inc., Santa Rosa, CA (US)

(72) Inventors: Keith Perkins, Santa Rosa, CA (US); Zachary Borglin, Petaluma, CA (US); Mark Stiger, Santa Rosa, CA (US); Julie Benton, Santa Rosa, CA (US); Steven Claessens, Santa Rosa, CA (US); Travis Rowe, Santa Rosa, CA (US); Mark Young, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 16/527,769

(22) Filed: Jul. 31, 2019

(65) Prior Publication Data
US 2021/0030526 A1 Feb. 4, 2021

(51) Int. Cl.
*A61F 2/06* (2013.01)
*A61F 2/07* (2013.01)
(Continued)

(52) U.S. Cl.
CPC .................. *A61F 2/06* (2013.01); *A61F 2/07* (2013.01); *A61F 2/856* (2013.01); *A61F 2/852* (2013.01);
(Continued)

(58) Field of Classification Search
CPC ........................... A61F 2002/061; A61F 2/856
See application file for complete search history.

(56) References Cited

U.S. PATENT DOCUMENTS

| | | | |
|---|---|---|---|
| 6,102,940 | A | 8/2000 | Robichon et al. |
| 6,641,606 | B2 | 11/2003 | Ouriel et al. |

(Continued)

FOREIGN PATENT DOCUMENTS

| | | |
|---|---|---|
| EP | 2525742 B1 | 11/2012 |
| EP | 2574306 A1 | 4/2013 |

(Continued)

OTHER PUBLICATIONS

U.S. Appl. No. 16/554,803, of Ashish Dhawan et al., titled "Use of Multiple Charged Ionic Compounds Derived From Polyamines for Waste Water Clarification", filed Aug. 29, 2019.

(Continued)

*Primary Examiner* — Leslie Lopez
(74) *Attorney, Agent, or Firm* — Brooks Kushman P.C.

(57) ABSTRACT

The techniques of this disclosure generally relate to a modular stent device including a main body configured to be deployed in the ascending aorta, a bypass gate configured to be deployed in the aorta, and a bifurcated contra limb. The bifurcated contra limb includes a single proximal limb that is bifurcated (split) into a first distal limb and a second distal limb. By forming the bifurcated contra limb to include a single proximal limb that is bifurcated into the distal limbs, guiding a guide wire into the relatively larger opening of bifurcated contra limb at a proximal end is simpler than guiding a guidewire into two smaller limbs extending distally from main body. Accordingly, cannulation of the bifurcated contra limb is relatively simple thus simplifying the procedure. In addition, the parallel design mimics anatomical blood vessel bifurcations to limit flow disruptions.

10 Claims, 10 Drawing Sheets

(51) Int. Cl.
*A61F 2/82* (2013.01)
*A61F 2/856* (2013.01)
*A61F 2/852* (2013.01)

(52) U.S. Cl.
CPC ... *A61F 2002/061* (2013.01); *A61F 2002/067* (2013.01); *A61F 2002/828* (2013.01); *A61F 2250/006* (2013.01)

(56) References Cited

U.S. PATENT DOCUMENTS

| | | | |
|---|---|---|---|
| 6,723,116 | B2 | 4/2004 | Taheri |
| 6,814,752 | B1 | 11/2004 | Chuter |
| 7,267,685 | B2 | 9/2007 | Butaric et al. |
| 8,545,549 | B2 | 10/2013 | Hartley et al. |
| 8,702,791 | B2 | 4/2014 | Kelly |
| 8,734,504 | B2 | 5/2014 | Kelly |
| 9,011,517 | B2 | 4/2015 | Hartley et al. |
| 9,101,456 | B2 | 8/2015 | Hartley et al. |
| 9,283,068 | B2 | 3/2016 | Kelly |
| 9,370,413 | B2 | 6/2016 | Kelly |
| 9,393,102 | B2 | 7/2016 | Kelly |
| 9,592,112 | B2 | 3/2017 | Arbefeuille et al. |
| 9,839,542 | B2 | 12/2017 | Bruszewski et al. |
| 9,861,505 | B2 | 1/2018 | Khoury |
| 9,949,818 | B2 | 4/2018 | Kelly |
| 9,980,832 | B2 | 5/2018 | Kelly |
| 9,993,330 | B2 | 6/2018 | Roeder |
| 10,231,822 | B2 | 3/2019 | Hartley |
| 2002/0058986 | A1 | 5/2002 | Landau et al. |
| 2002/0099441 | A1 | 7/2002 | Dehdashtian |
| 2003/0120330 | A1* | 6/2003 | Ouriel ............... A61F 2/07 623/1.14 |
| 2003/0130720 | A1 | 7/2003 | Depalma et al. |
| 2004/0117003 | A1 | 6/2004 | Ouriel et al. |
| 2005/0102018 | A1 | 5/2005 | Carpenter et al. |
| 2006/0155363 | A1 | 7/2006 | LaDuca et al. |
| 2006/0184228 | A1 | 8/2006 | Khoury |
| 2007/0168013 | A1 | 7/2007 | Douglas |
| 2007/0250154 | A1 | 10/2007 | Greenberg et al. |
| 2008/0097578 | A1 | 4/2008 | Erickson et al. |
| 2008/0147173 | A1 | 6/2008 | McIff et al. |
| 2009/0043373 | A1 | 2/2009 | Arnault De La Menardiere et al. |
| 2009/0125100 | A1 | 5/2009 | Mead |
| 2009/0306763 | A1 | 12/2009 | Roeder et al. |
| 2010/0100168 | A1 | 4/2010 | Chuter et al. |
| 2011/0196477 | A1 | 8/2011 | Ganesan et al. |
| 2011/0238160 | A1 | 9/2011 | Molony |
| 2012/0123527 | A1 | 5/2012 | Isch |
| 2012/0271401 | A1 | 10/2012 | Bruszewski et al. |
| 2013/0013050 | A1 | 1/2013 | Shalev et al. |
| 2013/0013052 | A1 | 1/2013 | Christiansen et al. |
| 2013/0274861 | A1* | 10/2013 | Kelly ............... A61F 2/95 623/1.13 |
| 2014/0172064 | A1 | 6/2014 | Kelly |
| 2015/0157446 | A1 | 6/2015 | Kelly |
| 2016/0287376 | A1 | 10/2016 | Kelly |
| 2016/0324626 | A1 | 11/2016 | Kelly |
| 2016/0367353 | A1 | 12/2016 | Kelly |
| 2017/0209254 | A1* | 7/2017 | Barthold ............... A61F 2/852 |
| 2017/0296324 | A1 | 10/2017 | Argentine |
| 2017/0340461 | A1 | 11/2017 | Varga |
| 2018/0071077 | A1 | 3/2018 | Argentine et al. |
| 2018/0153677 | A1 | 6/2018 | Perkins et al. |
| 2018/0235786 | A1 | 8/2018 | Kelly |
| 2018/0243076 | A1 | 8/2018 | Greenberg et al. |
| 2018/0325653 | A1 | 11/2018 | Kelly |
| 2019/0380851 | A1 | 12/2019 | Bertini et al. |

FOREIGN PATENT DOCUMENTS

| | | |
|---|---|---|
| EP | 3448313 B1 | 4/2020 |
| WO | 2014163957 A1 | 10/2014 |
| WO | 2019245624 A1 | 12/2019 |

OTHER PUBLICATIONS

PCT/US2020/023170, The International Search Report and the Written Opinion of the International Searching Authority, dated Jun. 30, 2020, 12 pages.
PCT/US2020/023176, The International Search Report and the Written Opinion of the International Searching Authority, dated Jun. 19, 2020, 15 pages.
International Search Report, Application No. PCT/US2019/024676, dated Jun. 17, 2019, pp. 1-14.
M. Lachat, "Nexus aortic arch stentgraft: Mid-term results", Leipzig Interventional Course 2017, UniversitatsSpital Zurich, Jan. 24-27, 2017, pp. 1-30, www.leipzig-interventional-course.com.
Jae Woong Lim et al., "Totally endocascular aortic arch repair by branched stent graft placement", Journal of Vascular Surgery Cases, Dec. 2015, pp. 279-282, vol. 1, No. 4.
W. Anthony Lee, Md., "The Bolton Medical Branched Thoracic Stent-Graft", Sponsored by Bolton Medical, Inc., pp. 1-6.
Michael D. Dake et al.," Thoracic Branch Endoprosthesis: Early Case Experience and the Clinical Trial", Supplement to Endovascular Today, Mar. 2017, pp. 21-24, vol. 16, No. 3.
Augusto D'Onofrio et al., "Endovascular treatment of aortic arch aneurysm with a single-branched double-stage stent graft", The Journal of Thoracic and Cardiovascular Surgery, Jul. 11, 2017, pp. e75-e77, vol. 154, No. 5.
Joseph Anderson, "Complete endovascular debranching of the aortic arch: A report of two cases", Vascular, Jul. 11, 2014, pp. 1-7, http://vas.sagepub.com/content/early/2014/07/11/ 1708538114542174, SAGE Publications.
Ciro Ferrer et al., "Endovascular repair of aortic arch disease with double inner branched thoracic stent graft: the Bolton perspective", The Journal of Cardiovascular Surgery, Aug. 2018, pp. 547-553, vol. 59 No. 4.
Stephan Haulon et al., "Global experience with an inner branched arch endograft", The Journal of Thoracic and Cardiovascular Surgery, 2014, pp. 1709-1716, vol. 148 No. 4.
Chen Huang et al., "Application of Unibody Single-Branch Endografts in Stanford Type B Dissections with Primary Entry Tear Adjacent to the Left Subclavian Artery: A Computed TomographyeBased Planning Study", Annals for Vascular Surgery, Aug. 2015, pp. 1174-1180, vol. 29 No. 6.
Himanshu J. Patel et al., "Branched Endovascular Therapy of the Distal Aortic Arch: Preliminary Results of the Feasibility Multicenter Trial of the Gore Thoracic Branch Endoprosthesis", Branched Aortic Arch Tevar Trial, The Society of Thoracic Surgeons, Mar. 22, 2016, pp. 1190-1198, Elsevier Ltd.
Vincent Riambau et al., "Application of the Bolton Relay Device for Thoracic Endografting in or Near the Aortic Arch", Aorta, Feb. 2015, pp. 16-24, vol. 3 Issue 1, Science International Corp., http://aorta.scienceinternational.org.
R. Spear et al., "Editor's Choice e Subsequent Results for Arch Aneurysm Repair with Inner Branched Endografts", Arch Aneurysm Endovascular Repair, Dec. 8, 2015, pp. 380-385., European Society for Vascular Surgery, Elsevier Ltd.
R. Spear et al., "Complex endovascular repair of postdissection arch and thoracoabdominal aneurysms", Society for Vascular Surgery, Journal of Vascular Surgery, Sep. 5, 2017, pp. 1-8, Elsevier Inc.
R. Spear et al., "Total Endovascular Treatment of Aortic Arch Disease Using an Arch Endograft With 3 Inner Branches", Journal of Endovascular Therapy, 2017, pp. 534-538, vol. 24(4), Sage Publications.
Zhong Gao Wang, "Single-Branch Endograft for Treating Stanford Type B Aortic Dissections With Entry Tears in Proximity to the Left Subclavian Artery", J Endovasc Ther, 2005, pp. 588-593, International Society of Endovascular Specialists.
U.S. Appl. No. 62/430,218, of Keith Perkins et al., titled "Modular Aortic Arch Prosthetic Assembly and Method of Use Thereof", filed Dec. 5, 2016.
U.S. Appl. No. 62/687,087, of Keith Perkins et al., titled "Modular Stent Device for Multiple Vessels", filed Jun. 19, 2018.

(56) References Cited

OTHER PUBLICATIONS

U.S. Appl. No. 15/830,221, of Keith Perkins et al., titled "Modular Aortic Arch Prosthetic Assembly and Method of Use Thereof", filed Dec. 4, 2017.
U.S. Appl. No. 16/367,906, of Keith Perkins et al., titled "Supra Aortic Access Modular Stent Assembly and Method", filed Mar. 28, 2019.
U.S. Appl. No. 16/367,922, of Keith Perkins et al., titled "Femoral Aortic Access Modular Stent Assembly and Method", filed Mar. 28, 2019.
U.S. Appl. No. 16/367,899, of Keith Perkins et al., titled "Modular Stent Device for Multiple Vessels and Method", filed Mar. 28, 2019.
U.S. Appl. No. 16/502,462, of Keith Perkins et al., titled "Single Multibranch Stent Device Assembly and Method", filed Jul. 3, 2019.
U.S. Appl. No. 16/585,768, of Keith Perkins et al., titled "Supra Aortic Access Trifurcated Modular Stent Assembly and Method", filed Sep. 27, 2019.
U.S. Appl. No. 16/554,813, of Keith Perkins et al., titled "Modular Multibranch Stent Assembly and Method", filed Aug. 29, 2019.
U.S. Appl. No. 16/585,722, of Keith Perkins et al., titled "Docking Graft for Placement of Parallel Distally Extending Grafts Assembly and Method", filed Sep. 27, 2019.
PCT/US2020/039169, The International Search Report and the Written Opinion of the International Searching Authority, dated Oct. 5, 2020, 16 pages.
PCT/US2020/044833, The International Search Report and the Written Opinion of the International Searching Authority, dated Nov. 16, 2020, 11 pages.
The International Search Report and the Written Opinion of the International Searching Authority for Application No. PCT/US2020/040866 dated Oct. 9, 2020, 9 Pages.

\* cited by examiner

MODULAR MULTIBRANCH STENT ASSEMBLY AND METHOD

FIELD

The present technology is generally related to an intravascular device and method. More particularly, the present application relates to a device for treatment of intra-vascular diseases.

BACKGROUND

Aneurysms, dissections, penetrating ulcers, intramural hematomas and/or transections may occur in blood vessels, and most typically occur in the aorta and peripheral arteries. The diseased region of the aorta may extend into areas having vessel bifurcations or segments of the aorta from which smaller "branch" arteries extend.

The diseased region of the aorta can be bypassed by use of a stent-graft placed inside the vessel spanning the diseased portion of the aorta, to seal off the diseased portion from further exposure to blood flowing through the aorta.

The use of stent-grafts to internally bypass the diseased portion of the aorta is not without challenges. In particular, care must be taken so that critical branch arteries are not covered or occluded by the stent-graft yet the stent-graft must seal against the aorta wall and provide a flow conduit for blood to flow past the diseased portion.

SUMMARY

The techniques of this disclosure generally relate to a modular stent device including a main body configured to be deployed in the ascending aorta, a bypass gate configured to be deployed in the aorta, and a bifurcated contra limb. The bifurcated contra limb includes a single proximal limb that is bifurcated (split) into a first distal limb and a second distal limb.

By forming the bifurcated contra limb to include a single proximal limb that is bifurcated into the distal limbs, guiding a guide wire into the relatively larger opening of bifurcated contra limb at a proximal end is simpler than guiding a guidewire into two smaller limbs extending distally from the main body. Accordingly, cannulation of the bifurcated contra limb is relatively simple thus simplifying the procedure. In addition, the parallel design mimics anatomical blood vessel bifurcations to limit flow disruptions.

In one aspect, the present disclosure provides an assembly including a first modular stent device having a main body configured to be deployed in the ascending aorta, a bypass gate configured to be deployed in the aorta, and a bifurcated contra limb. The bifurcated contra limb includes a proximal limb extending from the main body, a first distal limb extending from the proximal limb, and a second distal limb extending from the proximal limb. The first distal limb is connected to the second distal limb at a septum.

In another aspect, the present disclosure provides an assembly including a first modular stent device having a main body configured to be deployed in the ascending aorta, a bypass gate configured to be deployed in the aorta, and a bifurcated contra limb. The bifurcated contra limb includes a first distal limb configured to perfuse the brachiocephalic artery and a second distal limb configured to perfuse the left common carotid artery. The first distal limb is connected to the second distal limb at a septum.

In yet another aspect, the present disclosure provides a method including deploying a first modular stent device including deploying a main body of the first modular stent device in the ascending aorta, deploying a bypass gate of the first modular stent device in the aorta, and deploying a bifurcated contra limb of the first modular stent device proximal of the brachiocephalic artery. The bifurcated contra limb includes a first distal limb connected to a second distal limb at a septum.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
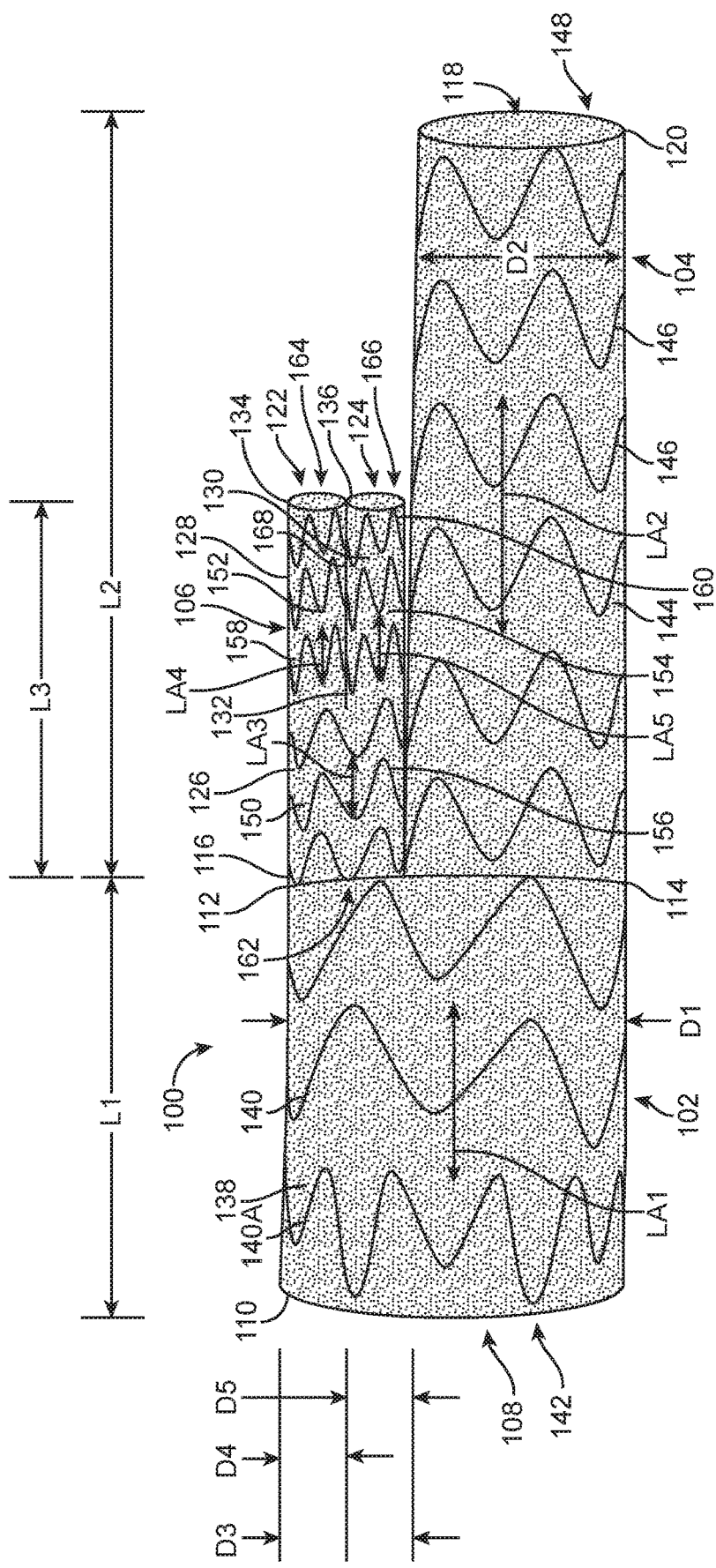
FIG. 1 is a side plan view of a modular stent device in accordance with one embodiment.
Figure 2:
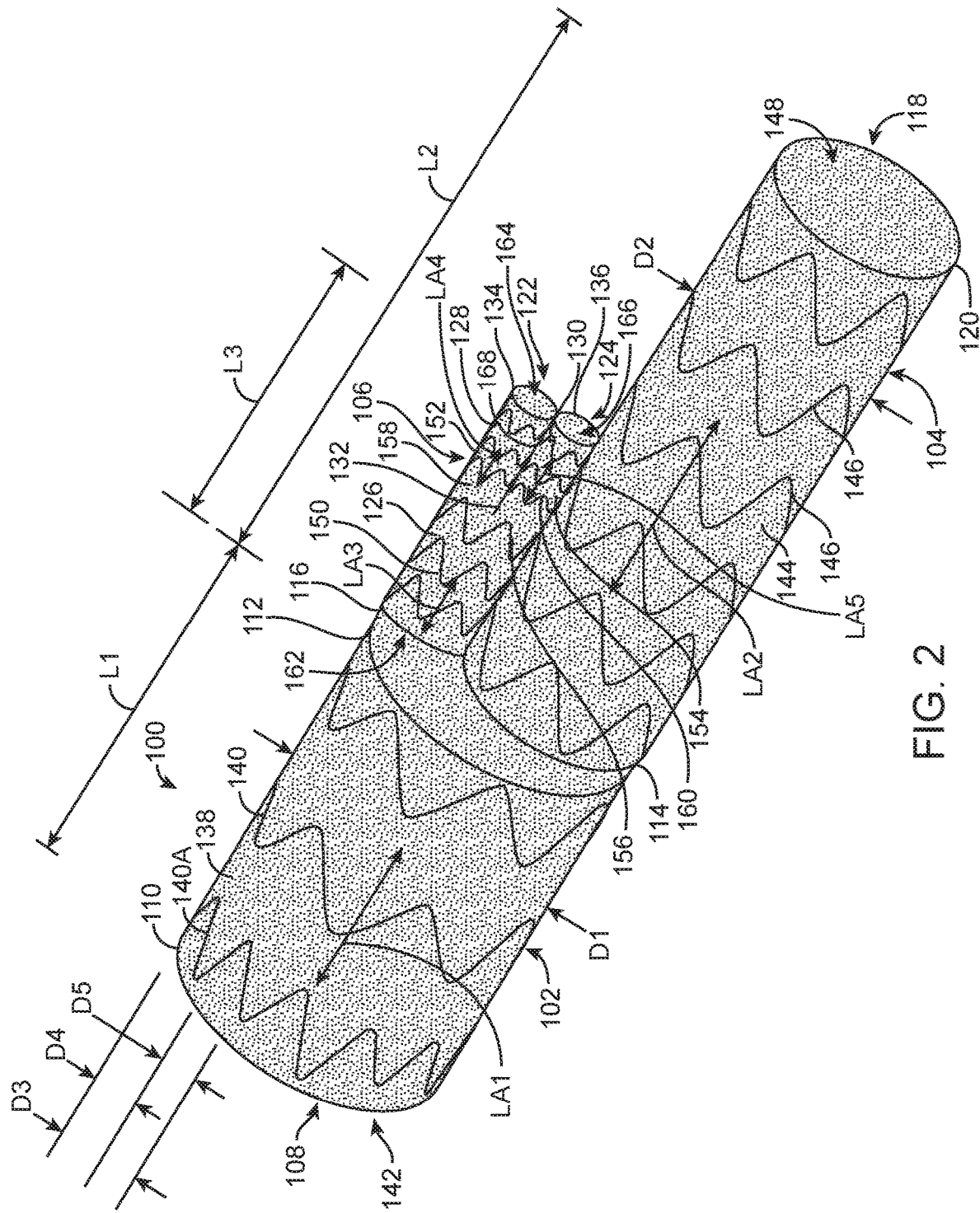
FIG. 2 is a perspective view of the modular stent device of FIG. 1 in accordance with one embodiment.

FIG. 1 is a side plan view of a modular stent device 100 in accordance with one embodiment. FIG. 2 is a perspective view of modular stent device 100 of FIG. 1 in accordance with one embodiment. Referring now to FIGS. 1 and 2 together, modular stent device 100, sometimes called a prosthesis or aortic arch prosthesis, includes a main body 102, a bypass gate 104 and a bifurcated contra limb 106.

In accordance with this embodiment, main body 102 includes a main body proximal opening 108 at a proximal end 110 of main body 102. A distal end 112 of main body 102 is coupled to a proximal end 114 of bypass gate 104 and a proximal end 116 of bifurcated contra limb 106. Bypass gate 104 includes a bypass gate distal opening 118 at a distal end 120 of bypass gate 104.

As used herein, the proximal end of a prosthesis such as modular stent device 100 is the end closest to the heart via the path of blood flow whereas the distal end is the end furthest away from the heart during deployment. In contrast and of note, the distal end of the catheter is usually identified to the end that is farthest from the operator/handle while the proximal end of the catheter is the end nearest the operator/handle.

For purposes of clarity of discussion, as used herein, the distal end of the catheter is the end that is farthest from the operator (the end furthest from the handle) while the distal end of modular stent device 100 is the end nearest the operator (the end nearest the handle), i.e., the distal end of the catheter and the proximal end of modular stent device 100 are the ends furthest from the handle while the proximal end of the catheter and the distal end of modular stent device 100 are the ends nearest the handle. However, those of skill in the art will understand that depending upon the access location, modular stent device 100 and the delivery system descriptions may be consistent or opposite in actual usage.

Bifurcated contra limb 106 is bifurcated from a single proximal opening at proximal end 116 to two distal openings 122, 124. More particularly, bifurcated contra limb 106 includes a single proximal limb 126 that is bifurcated (split) into a first distal limb 128 and a second distal limb 130 at a transition region 132 of bifurcated contra limb 106. More particularly, proximal limb 126 extends distally from proximal end 116 to transition region 132 and includes a single lumen. First distal limb 128 extends distally from transition region 132 to distal opening 122 at a distal end 134 of first distal limb 128 and includes a single lumen. Second distal limb 130 extends distally from transition region 132 to distal opening 124 at a distal end 136 of second distal limb 130 and includes a single lumen.

By forming bifurcated contra limb 106 to include a single proximal limb 126 that is bifurcated into distal limbs 128, 130, guiding a guide wire into the relatively larger opening of bifurcated contra limb 106 at proximal end 116 is simpler than guiding a guidewire into two smaller limbs extending distally from main body 102. Accordingly, cannulation of bifurcated contra limb 106 is relatively simple thus simplifying the procedure as discussed further below.

Main body 102 includes graft material 138 and one or more circumferential stents 140 coupled to graft material 138. Graft material 138 may be any suitable graft material, for example and not limited to, woven polyester, DACRON® material, expanded polytetrafluoroethylene, polyurethane, silicone, electro spun materials, or other suitable materials.

Circumferential stents 140 may be coupled to graft material 138 using stitching or other means. In the embodiment shown in FIGS. 1 and 2, circumferential stents 140 are coupled to an outside surface of graft material 138. However, circumferential stents 140 may alternatively be coupled to an inside surface of graft material 138.

Although shown with a particular number of circumferential stents 140, in light of this disclosure, those of skill in the art will understand that main body 102 may include a greater or smaller number of stents 140, e.g., depending upon the desired length of main body 102 and/or the intended application thereof.

Circumferential stents 140 may be any stent material or configuration. As shown, circumferential stents 140, e.g., self-expanding members, are preferably made from a shape memory material, such as nickel-titanium alloy (nitinol), and are formed into a zig-zag configuration. The configuration of circumferential stents 140 is merely exemplary, and circumferential stents 140 may have any suitable configuration, including but not limiting to a continuous or non-continuous helical configuration. In another embodiment, circumferential stents 140 are balloon expandable stents.

The circumferential stent 140A of circumferential stents 140 which is disposed at proximal end 110 is referred to herein as the proximal-most stent 140A. In the embodiment of FIGS. 1 and 2, proximal-most stent 140A extends only to the edge of graft material 138 in a closed-web configuration as shown. However, in another embodiment, proximal-most stent 140A extends proximally past the edge of graft material 138 in an open-web or uncovered configuration.

Further, main body 102 includes a longitudinal axis LA1. A lumen 142 is defined by graft material 138, and generally by main body 102. Lumen 142 extends generally parallel to longitudinal axis LA1 and between proximal opening 108 and distal end 112 of main body 102. Graft material 138 is cylindrical having a substantially uniform diameter in this embodiment. However, in other embodiments, graft material 138 varies in diameter.

Bypass gate 104 includes graft material 144 and one or more circumferential stents 146 coupled to graft material 144. Graft material 144 may be any suitable graft material, for example and not limited to, woven polyester, DACRON® material, expanded polytetrafluoroethylene, polyurethane, silicone, electro spun materials, or other suitable materials.

Circumferential stents 146 may be coupled to graft material 144 using stitching or other means. In the embodiment shown in FIGS. 1 and 2, circumferential stents 146 are coupled to an outside surface of graft material 144. However, circumferential stents 146 may alternatively be coupled to an inside surface of graft material 144.

Although shown with a particular number of circumferential stents 146, in light of this disclosure, those of skill in the art will understand that bypass gate 104 may include a greater or smaller number of stents 146, e.g., depending upon the desired length of bypass gate 104 and/or the intended application thereof.

Circumferential stents 146 may be any stent material or configuration. As shown, circumferential stents 146, e.g., self-expanding members, are preferably made from a shape memory material, such as nickel-titanium alloy (nitinol), and are formed into a zig-zag configuration. The configuration of circumferential stents 146 is merely exemplary, and circumferential stents 146 may have any suitable configuration, including but not limiting to a continuous or non-continuous helical configuration. In another embodiment, circumferential stents 146 are balloon expandable stents.

Further, bypass gate 104 includes a longitudinal axis LA2. A lumen 148 is defined by graft material 144, and generally by bypass gate 104. Lumen 148 extends generally parallel to longitudinal axis LA2 and between proximal end 114 and distal opening 118 of bypass gate 104. Graft material 144 is cylindrical having a substantially uniform diameter in this embodiment. However, in other embodiments, graft material 144 varies in diameter.

As set forth above, bifurcated contra limb 106 includes proximal limb 126, first distal limb 128, and second distal limb 130. Limbs 126, 128, 130 include graft materials 150, 152, 154 and one or more circumferential stents 156, 158, 160 coupled to graft materials 150, 152, 154, respectively. Graft materials 150, 152, 154 may be any suitable graft material, for example and not limited to, woven polyester, DACRON® material, expanded polytetrafluoroethylene, polyurethane, silicone, electro spun materials, or other suitable materials.

Circumferential stents 156, 158, 160 may be coupled to graft materials 150, 152, 154, respectively, using stitching or other means. In the embodiment shown in FIGS. 1 and 2, circumferential stents 156, 158, 160 are coupled to an outside surface of graft materials 150, 152, 154, respectively. However, circumferential stents 156, 158, 160 may alternatively be coupled to an inside surface of graft materials 150, 152, 154, respectively.

Although shown with a particular number of circumferential stents 156, 158, 160, in light of this disclosure, those of skill in the art will understand that limbs 126, 128, 130 may include a greater or smaller number of stents 156, 158, 160, e.g., depending upon the desired length of limbs 126, 128, 130 and/or the intended application thereof.

Circumferential stents 156, 158, 160 may be any stent material or configuration. As shown, circumferential stents 156, 158, 160, e.g., self-expanding members, are preferably made from a shape memory material, such as nickel-titanium alloy (nitinol), and are formed into a zig-zag configuration. The configuration of circumferential stents 156, 158, 160 is merely exemplary, and circumferential stents 156, 158, 160 may have any suitable configuration, including but not limiting to a continuous or non-continuous helical configuration. In another embodiment, circumferential stents 156, 158, 160 are balloon expandable stents.

Further, proximal limb 126 includes longitudinal axis LA3. A lumen 162 is defined by graft material 150, and generally by proximal limb 126. Lumen 162 extends generally parallel to longitudinal axis LA3 and between proximal end 116 and transition region 132 of bifurcated contra limb 106. Graft material 150 is cylindrical having a substantially uniform diameter in this embodiment. However, in other embodiments, graft material 150 varies in diameter.

Further, first distal limb 128 includes longitudinal axis LA4. A lumen 164 is defined by graft material 152, and generally by first distal limb 128. Lumen 164 extends generally parallel to longitudinal axis LA4 and between transition region 132 and distal opening 122 of first distal limb 128. Graft material 152 is cylindrical having a substantially uniform diameter in this embodiment. However, in other embodiments, graft material 152 varies in diameter.

Second distal limb 130 includes longitudinal axis LA5. A lumen 166 is defined by graft material 154, and generally by second distal limb 130. Lumen 166 extends generally parallel to longitudinal axis LA5 and between transition region 132 and distal opening 124 of second distal limb 130. Graft material 154 is cylindrical having a substantially uniform diameter in this embodiment. However, in other embodiments, graft material 154 varies in diameter.

In one embodiment, first distal limb 128 is connected to second distal limb 130 at a septum 168. For example, graft materials 150, 152, 154 are a single piece of graft material that is sewn or otherwise attached together at septum 168 to define limbs 128, 130. However, in another embodiment, limbs 128, 130 are not attached to one another such that limb 128 can be spread or moved apart from limb 130.

Generally, main body 102 is bifurcated at distal end 112 into bypass gate 104 and bifurcated contra limb 106. More particularly, lumen 142 of main body 102 is bifurcated into lumen 148 of bypass gate 104 and lumen 162 of proximal limb 126. Lumen 162 of proximal limb 126 is bifurcated into lumen 164 of first distal limb and lumen 166 of second distal limb 130.

In one embodiment, graft materials 138, 144, 150, 152, 154 may be the same graft material, e.g., may be a single piece of graft material cut and sewn. However, in other embodiments, one or more of graft materials 138, 144, 150, 152, 154 may be different than the others of graft materials 138, 144, 150, 152, 154, e.g., different graft materials are cut and sewn together.

In the relaxed configuration (unstressed) of modular stent device 100 as illustrated in FIGS. 1 and 2, longitudinal axes LA1, LA2, LA3, LA4, LA5 are parallel with one another such that bypass gate 104 and bifurcated contra limb 106 extend distally from main body 102 and distal limbs 128, 130 extend distally from proximal limb 126.

Further, longitudinal axis LA4 of first distal limb 128 is radially outward of longitudinal axis LA5 of second distal limb 130. In other words, second distal limb 130 is radially inward of first distal limb 128. Second distal limb 130 is located between bypass gate 104 and first distal limb 128. However, in other embodiments, other orientations of distal limbs 128, 130 relative to bypass gate 104 are used depending upon the particular application.

Main body 102 has first diameter D1, bypass gate 104 has second diameter D2, and bifurcated contra limb 106, e.g., proximal limb 126, has third diameter D3. In accordance with this embodiment, first diameter D1 is greater than second diameter D2. Further, second diameter D2 is greater than third diameter D3. In accordance with this embodiment, first diameter D1 is greater than second diameter D2 combined with third diameter D3 (D1>D2+D3) such that bypass gate 104 and bifurcated contra limb 106 are located within an imaginary cylinder defined by graft material 138 of main body 102 extended in the distal direction.

Further, first distal limb 128 has a fourth diameter D4 and second distal limb 130 has fifth diameter D5. In accordance with this embodiment, third diameter D3 of proximal limb 126 is greater than either of fourth diameter D4 and fifth diameter D5. The parallel design mimics anatomical blood vessel bifurcations to limit flow disruptions.

In one embodiment, first diameter D1 is greater than second diameter D2 combined with third diameter D3 (D1>D2+D3) at distal end 112 and proximal ends 114, 116, sometimes called the main transition region. However, main body 102, bypass gate 104 and/or bifurcated contra limb 106, flare or taper away from the main transition region in accordance with one embodiment, so D1>D2+D3 at the main transition region but is not necessarily correct in regions away from the main transition region.

Stated another way, the main transition region from main body 102 to bifurcated contra limb 106 and bypass gate 104 does not exceed first diameter D1 of main body 102. This insures bifurcated contra limb 106 and bypass gate 104 don't crush each other or negatively impact flow in any way. By avoiding having bifurcated contra limb 106 and bypass gate 104 extend out wider than main body 102, a good seal of stents 140 of main body 102 against the aorta is insured and type I endoleaks are minimized or avoided.

In accordance with one embodiment, the main transition region between main body 102 and bifurcated contra limb 106 and bypass gate 104 is fully supported by one or more supporting stents, e.g., stents 140, 146, 156, to prevent kinking in angled anatomy. Absent the supporting stents, modular stent device 100 may be predispose to kinking in type III arches or gothic arches.

Main body 102 has a first length L1 in a direction parallel to the longitudinal axis LA1, bypass gate 104 has a second length L2 in a direction parallel to the longitudinal axis LA2, and bifurcated contra limb 106 has a third length L3 in a direction parallel to the longitudinal axes LA3, LA4, LA5. In accordance with this embodiment, third length L3 is less than second length L2 such that distal openings 122, 124 of bifurcated contra limb 106 are proximal to distal opening 118 of bypass gate 104. Generally, bifurcated contra limb 106 is shorter than bypass gate 104. Distal openings 122, 124 of bifurcated contra limb 106 are aligned and coplanar in accordance with this embodiment.

Bifurcated contra limb 106 is configured to exert a higher radial force than the radial force of bypass gate 104. As used herein, "radial force" includes both a radial force exerted during expansion/deployment as well as a chronic radial force continuously exerted after implantation such that a scaffold has a predetermined compliance or resistance as the surrounding native anatomy, e.g., the aorta, expands and contracts during the cardiac cycle. The radial force of bypass gate 104 is configured to be lower than that of bifurcated contra limb 106 order to avoid collapse of bifurcated contra limb 106 when bypass gate 104 is deployed against and adjacent thereof and thus maintain perfusion of the brachiocephalic artery and left common carotid artery as discussed further below.

To configure bypass gate 104 and bifurcated contra limb 106 with differing relative radial forces, circumferential stents 156, 158, 160 of bifurcated contra limb 106 be constructed with relatively thicker and/or shorter segments of material than circumferential stents 146 of bypass gate 104. Shorter and/or thicker circumferential stents 156, 158, 160 have less flexibility but greater radial force to ensure that circumferential stents 146 of bypass gate 104 do not collapse lumens 162, 164, 166 of bifurcated contra limb 106. Other variations or modification of circumferential stents 146, 156, 158, 160 may be used to achieve relative radial forces in other embodiments.

Figure 3:
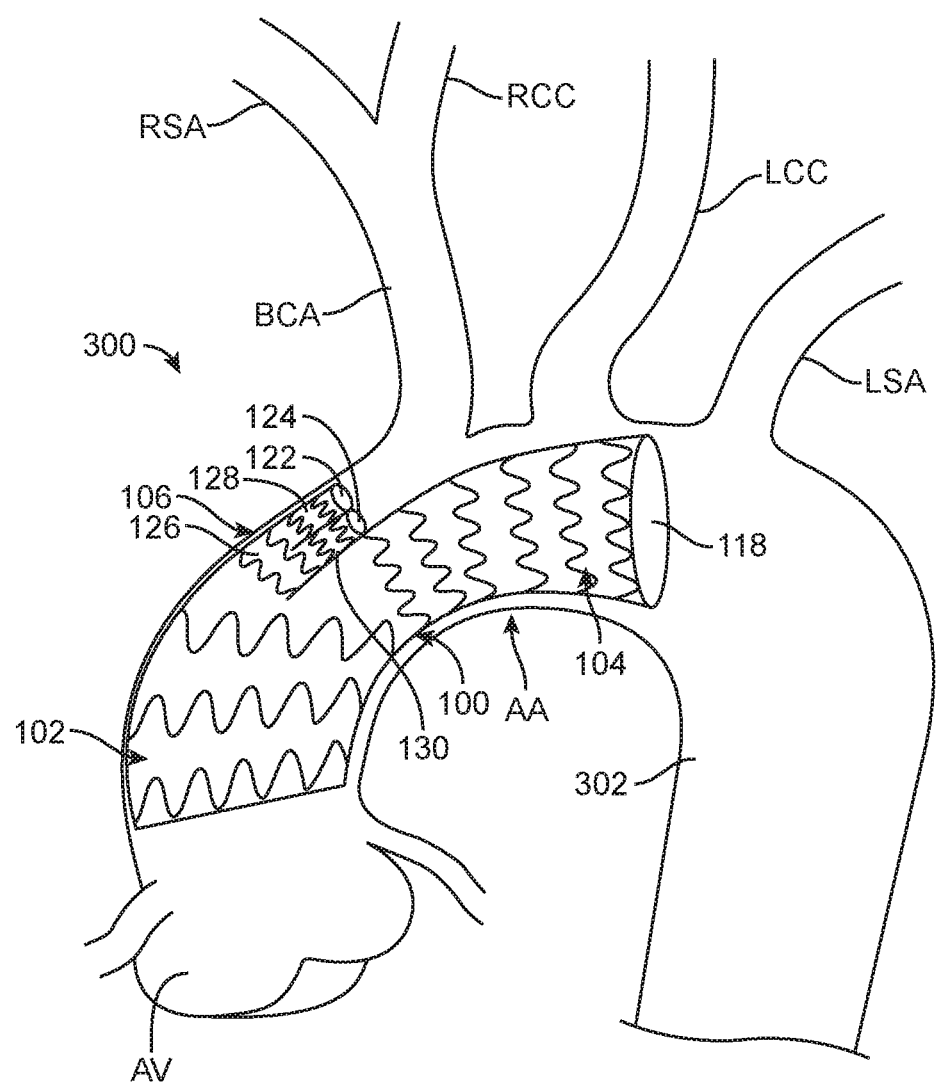
FIG. 3 is a cross-sectional view of a vessel assembly including the modular stent device of FIGS. 1 and 2 during deployment in accordance with one embodiment.

FIG. 3 is a cross-sectional view of a vessel assembly 300 including modular stent device 100 of FIGS. 1 and 2 during deployment in accordance with one embodiment. Referring to FIGS. 1, 2 and 3 together, the thoracic aorta 302 has numerous arterial branches. The arch AA of the aorta 302 has three major branches extending therefrom, all of which usually arise from the convex upper surface of the arch AA. The brachiocephalic artery BCA originates anterior to the trachea. The brachiocephalic artery BCA divides into two branches, the right subclavian artery RSA (which supplies blood to the right arm) and the right common carotid artery RCC (which supplies blood to the right side of the head and neck). The left common carotid artery LCC artery arises from the arch AA of the aorta 302 just to the left of the origin of the brachiocephalic artery BCA. The left common carotid artery LCC supplies blood to the left side of the head and neck. The third branch arising from the aortic arch AA, the left subclavian artery LSA, originates behind and just to the left of the origin of the left common carotid artery LCC and supplies blood to the left arm.

However, a significant proportion of the population has only two great branch vessels coming off the aortic arch AA while others have four great branch vessels coming of the aortic arch AA. Accordingly, although a particular anatomical geometry of the aortic arch AA is illustrated and discussed, in light of this disclosure, those of skill in the art will understand that the geometry of the aortic arch AA has anatomical variations and that the various structures as disclosed herein would be modified accordingly.

Aneurysms, dissections, penetrating ulcers, intramural hematomas and/or transections, generally referred to as a diseased region of the aorta 302, may occur in the aorta arch AA and the peripheral arteries BCA, LCC, LSA. For example, thoracic aortic aneurysms include aneurysms present in the ascending thoracic aorta, the aortic arch AA, and one or more of the branch arteries BCA, LCC, LSA that emanate therefrom. Thoracic aortic aneurysms also include aneurysms present in the descending thoracic aorta and branch arteries that emanate therefrom. Accordingly, the aorta 302 as illustrated in FIG. 3 has a diseased region similar to any one of those discussed above which will be bypassed and excluded using modular stent device 100 as discussed below.

To deploy modular stent device 100, a guide wire is introduced via femoral access. In one particular embodiment, the guidewire is inserted into the femoral artery and routed up through the abdominal aorta, and into the thoracic aorta.

A delivery system including modular stent device 100 is introduced via femoral access and is advanced into the ascending aorta 302 over the guidewire. The delivery system is positioned at the desired location such that the position of modular stent device 100 is in the ascending aorta near the aortic valve AV.

A delivery sheath of the delivery system is withdrawn to expose main body 102, bifurcated contra limb 106, and bypass gate 104. This deploys main body 102, bifurcated contra limb 106, and bypass gate 104.

Bifurcated contra limb 106 is opened thus insuring perfusion to distal territories, e.g., including the brachiocephalic artery BCA and the left common carotid artery LCC. In accordance with this embodiment, distal openings 122, 124 of bifurcated contra limb 106 are proximal to both the brachiocephalic artery BCA and the left common carotid artery LCC allowing easy cannulation thereof as discussed below.

In accordance with this embodiment, distal opening 118 of bypass gate 104 is proximal to the left subclavian artery LSA thus insuring perfusion thereof.

Figure 4:
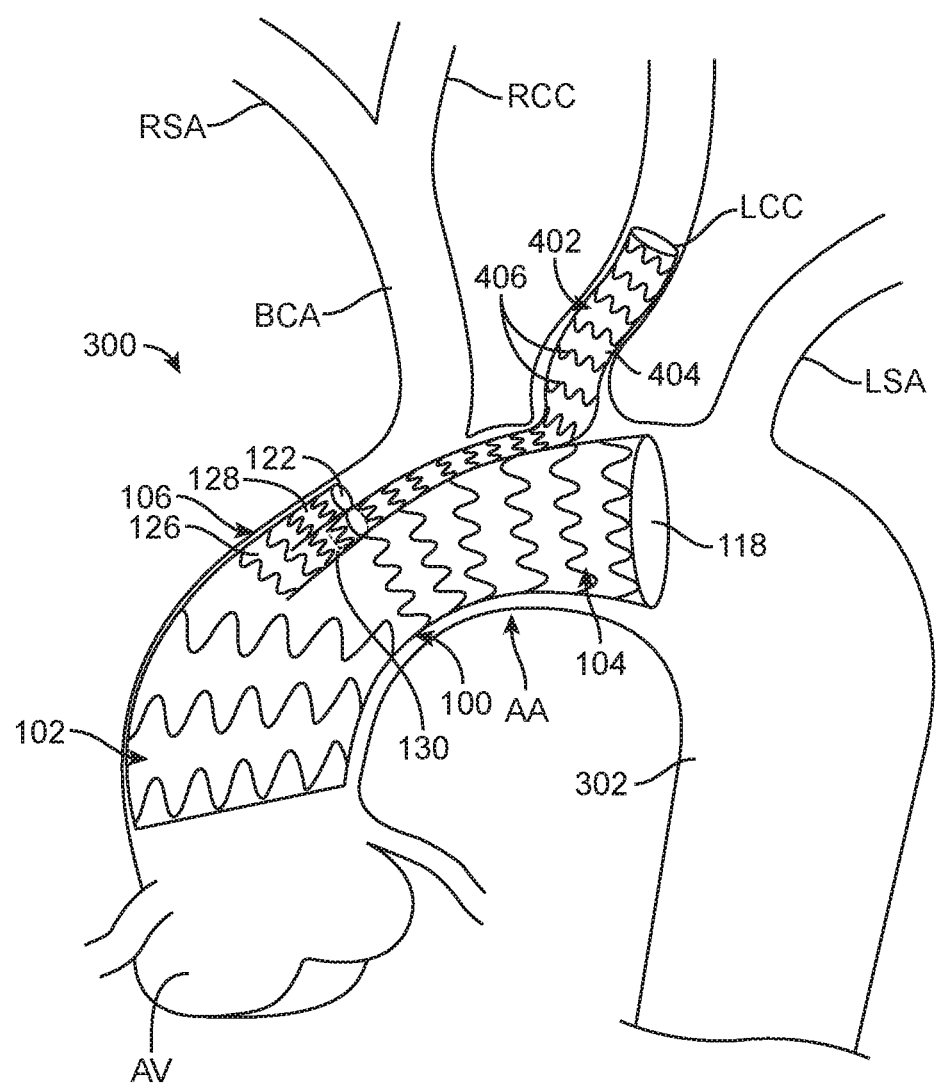
FIG. 4 is a cross-sectional view of the vessel assembly of FIG. 3 at a later stage during deployment of a first bridging stent graft in accordance with one embodiment.

FIG. 4 is a cross-sectional view of vessel assembly 300 of FIG. 3 at a later stage during deployment of a first bridging stent graft 402, sometimes called a bridging stent, in accordance with one embodiment. Referring to FIG. 4, bridging stent graft 402 is deployed within second distal limb 130 and the left common carotid artery LCC. More particularly, bridging stent graft 402 self-expands (or is balloon expanded) to be anchored within second distal limb 130 and the left common carotid artery LCC.

Bridging stent graft 402 includes graft material 404 and one or more circumferential stents 406. Upon deployment of bridging stent graft 402, blood flow into bifurcated contra limb 106 and second distal limb 130 is bridged and passed into the left common carotid artery LCC through bridging stent graft 402.

Figure 5:
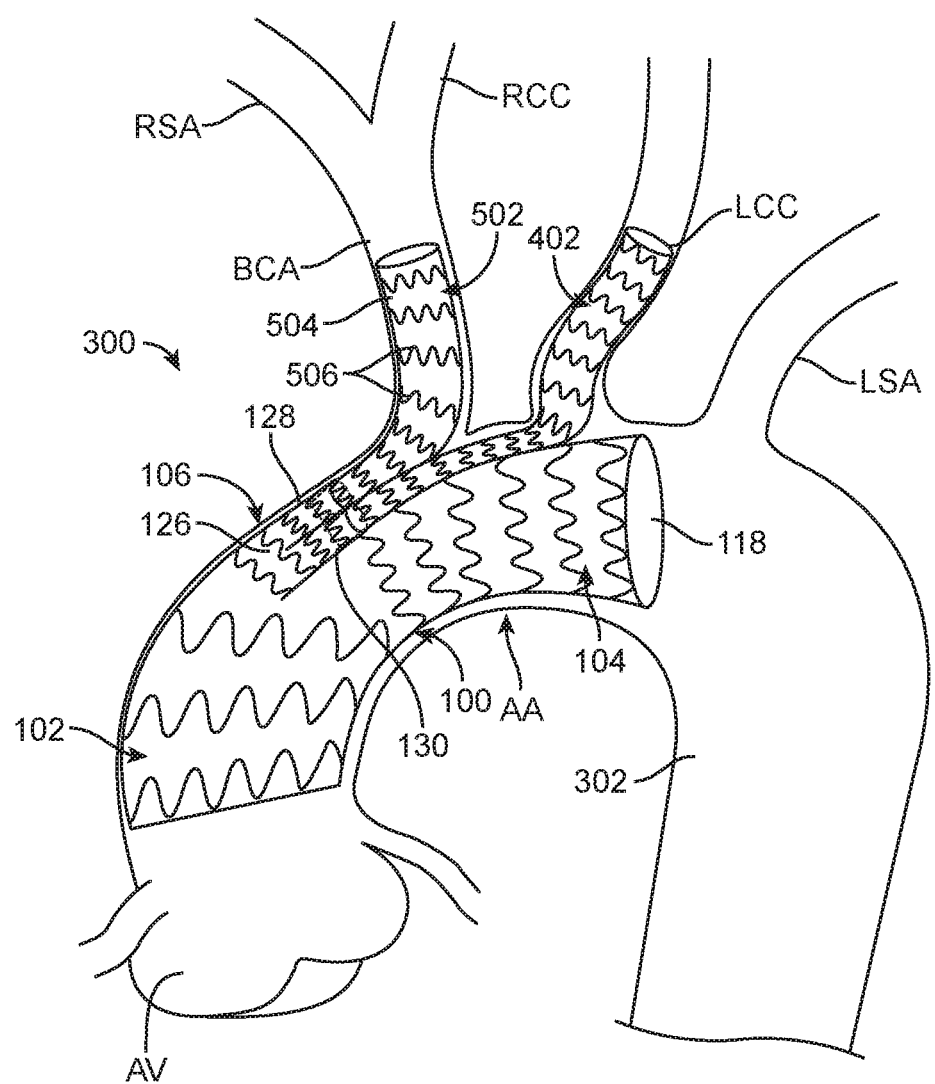
FIG. 5 is a cross-sectional view of the vessel assembly of FIG. 4 at a later stage during deployment of a second bridging stent graft in accordance with one embodiment.

FIG. 5 is a cross-sectional view of vessel assembly 300 of FIG. 4 at a later stage during deployment of a second bridging stent graft 502, sometimes called a bridging stent, in accordance with one embodiment. Referring to FIG. 5, bridging stent graft 502 is deployed within first distal limb 128 and the brachiocephalic artery BCA. More particularly, bridging stent graft 502 self-expands (or is balloon expanded) to be anchored within first distal limb 128 and the brachiocephalic artery BCA.

Bridging stent graft 502 includes graft material 504 and one or more circumferential stents 506. Upon deployment of bridging stent graft 502, blood flow into bifurcated contra limb 106 and first distal limb 128 is bridged and passed into the brachiocephalic artery BCA through bridging stent graft 502.

Bridging stent grafts 402, 502 are deployed from femoral access or supra aortic access in various embodiments. When deployed from femoral access, a guidewire is introduced via femoral access. In one particular embodiment, the guidewire is inserted into the femoral artery and routed up through the abdominal aorta, and into distal opening 118 of bypass gate 104. The guidewire is then manipulated into proximal limb 126 of bifurcated contra limb 106. As diameter D3 of bifurcated contra limb 106 is relatively large as compared to diameters D4, D5 of distal limbs 128, 130, respectively, guiding of the guidewire is simplified. The guidewire is passed out of distal opening 124 of second distal limb 130 and into the left common carotid artery LCC during deployment of bridging stent graft 402. Alternatively, the guidewire is passed out of distal opening 122 of first distal limb 128 and into the brachiocephalic artery BCA during deployment of bridging stent graft 502.

A delivery system including bridging stent graft 402 or 502 is introduced via femoral access and is advanced over the guidewire. The delivery system is positioned at the desired location. A delivery sheath of the delivery system is withdrawn to expose bridging stent graft 402 or 502. This deploys bridging stent graft 402 or 502. The procedure is then repeated to deploy the other of bridging stent graft 402 or 502.

When deployed from supra aortic access, a guidewire is introduced via supra aortic access, e.g., through the left common carotid artery LCC or the brachiocephalic artery BCA. The guidewire is then manipulated from the left common carotid artery LCC and into distal opening 124 of second distal limb 130 for deployment of bridging stent graft 402. Alternatively, the guidewire is manipulated from the brachiocephalic artery BCA and into distal opening 122 of first distal limb 128 for deployment of bridging stent graft 502.

A delivery system including bridging stent graft 402 or 502 is introduced via supra aortic access and is advanced over the guidewire. The delivery system is positioned at the desired location. A delivery sheath of the delivery system is withdrawn to expose bridging stent graft 402 or 502. This deploys bridging stent graft 402 or 502. The procedure is then repeated to deploy the other of bridging stent graft 402 or 502.

Figure 6:
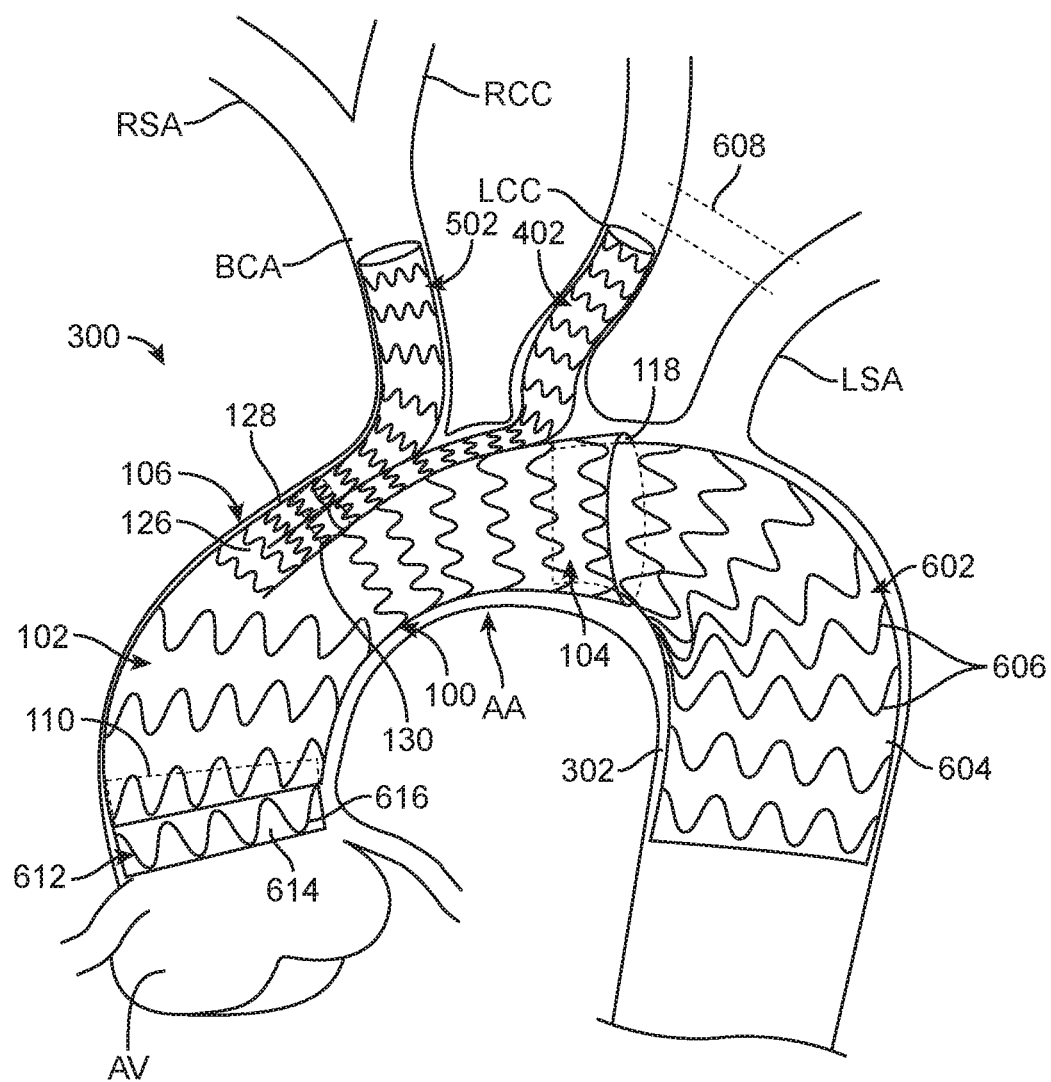
FIG. 6 is a cross-sectional view of the vessel assembly of FIG. 5 at a later stage during deployment of a tube graft into the modular stent device in accordance with one embodiment.

FIG. 6 is a cross-sectional view of vessel assembly 300 of FIG. 5 at a later stage during deployment of a tube graft 602 into modular stent device 100 in accordance with one embodiment. To deploy tube graft 602, a delivery system including tube graft 602 is advanced via femoral access into distal opening 118 of bypass gate 104. Once positioned, a delivery sheath of the delivery system is withdrawn to expose tube graft 602. Upon being exposed, tube graft 602 self expands (or is balloon expanded) into bypass gate 104 and the aorta 302 and is attached thereto.

Tube graft 602 includes graft material 604 and one or more circumferential stents 606. Graft material 604 is similar to or identical to any one of the graft materials as discussed. In addition, circumferential stents 606 are similar to or identical to any one of circumferential stents as discussed above.

Upon completion of deployment of tube graft 602, blood flows through bypass gate 104 and tube graft 602 thus perfusing the distal territories. At the same time, bypass gate 104 and tube graft 602 exclude any overlapped diseased regions of the aorta 302.

In accordance with this embodiment, tube graft 602 overlaps, excludes and thus occludes the left subclavian artery LSA. In accordance with this embodiment, a bypass 608 provides perfusion to the left subclavian artery LSA. Illustratively, bypass 608 provides perfusion of the left subclavian artery LSA from the left common carotid artery LCC.

Bypass 608 is surgically inserted during the same procedure as deployment of modular stent device 100 and tube graft 602. However, in another embodiment, bypass 608 is surgically inserted prior to deployment of modular stent device 100 and tube graft 602, e.g., to simplify the procedure.

In one embodiment, tube graft 602 is unnecessary and not deployed. For example, modular stent device 100 provide sufficient exclusion of the diseased region of the aorta 302. Accordingly, tube graft 602 is unnecessary and not deployed. In the case where tube graft 602 is not deployed, perfusion is maintained to the left subclavian artery LSA and thus bypass 608 is unnecessary.

Further, as illustrated in FIG. 6, optionally, a proximal cuff 612 is coupled to main body 102 of modular stent device 100 and extend proximately therefrom. For example, proximal cuff 612 is deployed in the event that proximal end 110 of main body 102 is deployed distally from the aortic valve AV to extend between the desired deployment location and proximal end 110 of main body 102. Proximal cuff 612 is optional and in one embodiment is not deployed or used.

Proximal cuff 612 includes graft material 614 and one or more circumferential stents 616. Graft material 614 is similar to or identical to any one of the graft materials as discussed above. In addition, circumferential stents 616 are similar to or identical to any one of circumferential stents as discussed above.

Figure 7:
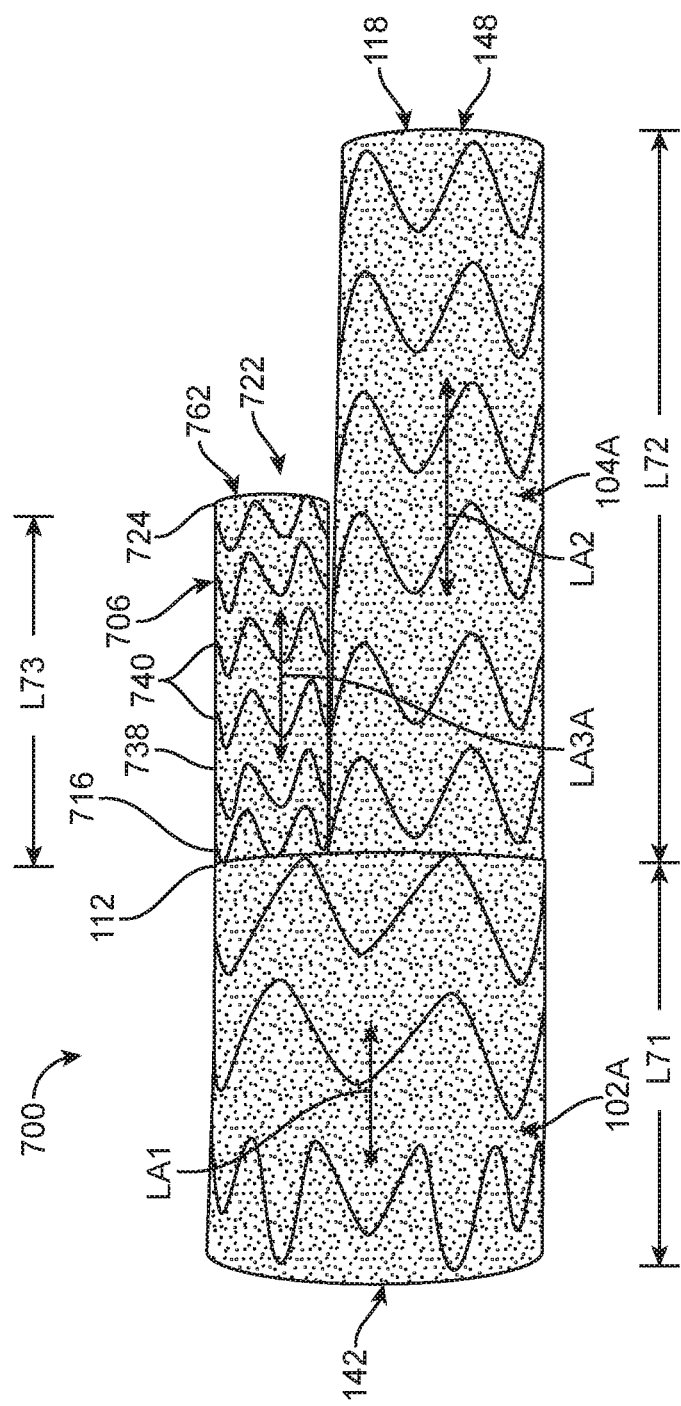
FIG. 7 is a side plan view of a second modular stent device in accordance with one embodiment.
Figure 8:
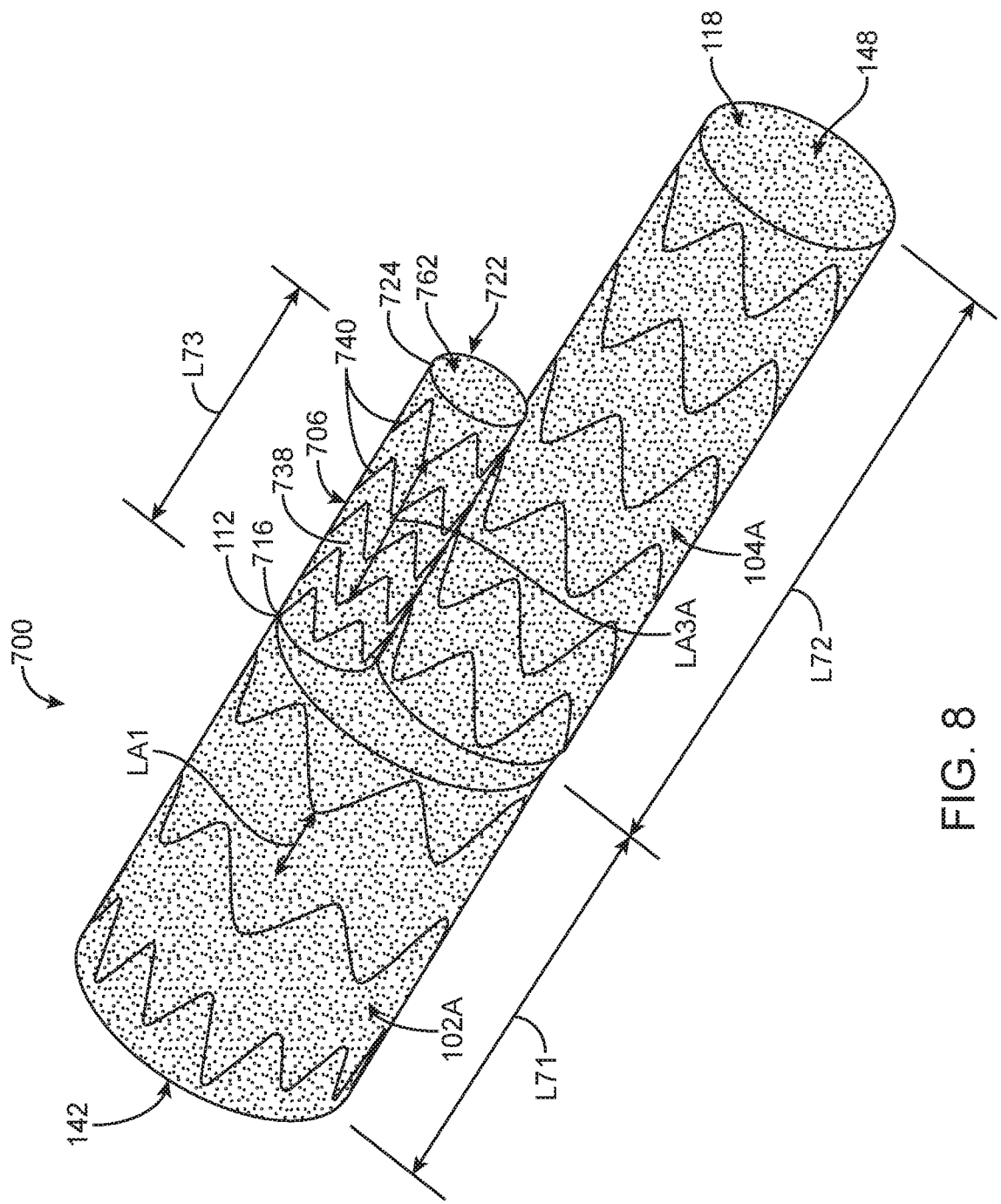
FIG. 8 is a perspective view of the second modular stent device of FIG. 7 in accordance with one embodiment.

FIG. 7 is a side plan view of a second modular stent device 700 in accordance with one embodiment. FIG. 8 is a perspective view of second modular stent device 700 of FIG. 7 in accordance with one embodiment. Referring now to FIGS. 1, 2, 7, and 8 together, second modular stent device 700 includes a main body 102A, a bypass gate 104A and an artery limb 706. Second modular stent device 700 is similar to modular stent device 100 as described above, and only the significant differences are discussed below. More particularly, main body 102A and bypass gate 104A of second modular stent device 700 are similar to main body 102 and bypass gate 104 of modular stent device 100, and so the description thereof is not repeated for simplicity.

Referring now to second modular stent device 700 as illustrated in FIGS. 7 and 8 together, distal end 112 of main body 102A is coupled to a proximal end 716 of artery limb 706. Artery branch 706 includes a leg distal opening 722 at a distal end 724 of artery limb 706.

Artery branch 706 includes graft material 738 and one or more circumferential stents 740 coupled to graft material 738. Graft material 738 may be any suitable graft material such as those discussed above. Further, circumferential stents 140 may be any stent material or configuration as described above.

Circumferential stents 740 may be coupled to graft material 738 using stitching or other means. In the embodiment shown in FIGS. 7 and 8, circumferential stents 740 are coupled to an outside surface of graft material 738. However, circumferential stents 740 may alternatively be coupled to an inside surface of graft material 738.

Although shown with a particular number of circumferential stents 740, in light of this disclosure, those of skill in the art will understand that artery branch 706 may include a greater or smaller number of stents 740, e.g., depending upon the desired length of artery branch 706 and/or the intended application thereof.

Further, artery branch 706 includes longitudinal axis LA3A. A lumen 762 is defined by graft material 738, and generally by artery limb 706. Lumen 762 extends generally parallel to longitudinal axis LA3A and between proximal end 716 and distal opening 722 of artery limb 706. Graft material 738 is cylindrical having a substantially uniform diameter in this embodiment. However, in other embodiments, graft material 738 varies in diameter.

Generally, main body 102A is bifurcated at distal end 112 into bypass gate 104A and artery limb 706. More particularly, lumen 142 of main body 102A is bifurcated into lumen 148 of bypass gate 104A and lumen 762 of artery limb 706.

Main body 102A has a first length L71 in a direction parallel to the longitudinal axis LA1 of main body 102A, bypass gate 104A has a second length L72 in a direction parallel to the longitudinal axis LA2 of bypass gate 104A, and artery branch 706 has a third length L73 in a direction parallel to the longitudinal axis LA3A of artery limb 706. In accordance with this embodiment, third length L73 is less than second length L72 such that distal opening 722 of artery branch 706 is proximal to distal opening 118 of bypass gate 104A. Generally, artery branch 706 is shorter than bypass gate 104A.

Artery branch 706 is configured to exert a higher radial force than the radial force of bypass gate 104A to avoid collapse of artery branch 706 by bypass gate 104A. Further descriptions of a device similar to second modular stent device 700 are set forth in Perkins et al, U.S. patent application Ser. No. 16/367,889, entitled "MODULAR STENT DEVICE FOR MULTIPLE VESSELS AND METHOD", filed on Mar. 28, 2019, and issued as U.S. Pat. No. 11,304,794 on Apr. 19, 2022, and Perkins et al, U.S. patent application Ser. No. 16/367,922, and issued as U.S. Pat. No. 11,083,605 on Aug. 10, 2021, entitled "FEMORAL AORTIC ACCESS MODULAR STENT ASSEMBLY AND METHOD, filed on Mar. 28, 2019, which are both herein incorporated by reference in their entireties.

Figure 9:
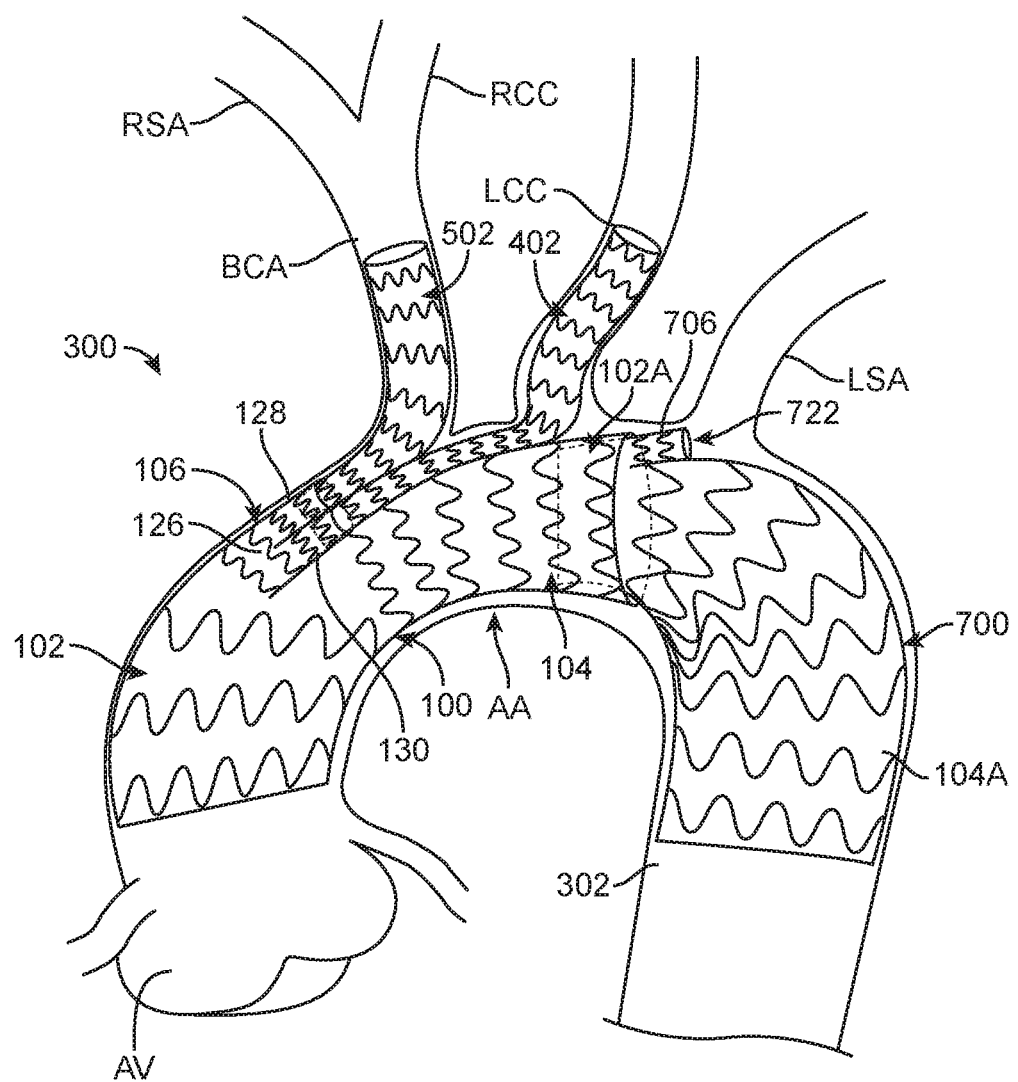
FIG. 9 is a cross-sectional view of the vessel assembly of FIG. 5 at a later stage during deployment of the second modular stent device of FIGS. 7 and 8 into the modular stent device in accordance with one embodiment.

FIG. 9 is a cross-sectional view of vessel assembly 300 of FIG. 5 at a later stage during deployment of second modular stent device 700 of FIGS. 7 and 8 into modular stent device 100 in accordance with one embodiment. In accordance with this embodiment, second modular stent device 700 is deployed within bypass gate 104 of modular stent device 100 via femoral access in a manner similar to that discussed above regarding modular stent device 100.

More particularly, main body 102A of second modular stent device 700 is located within bypass gate 104 of modular stent device 100, sometimes called a first modular stent device 100. Bypass gate 104A of second modular stent device 700 is located within aorta 302 and arranged to point away and distally from first modular stent device 100. In accordance with this embodiment, distal opening 722 of artery branch 706 of second modular stent device 700 is proximal to the left subclavian artery LSA allowing easy cannulation thereof as discussed below.

In accordance with this embodiment, blood flow enters second modular stent device 700 through main gate 102A, and exits through bypass gate 104A and artery branch 706. Accordingly, blood flows through artery branch 706 and perfusion of the left subclavian artery LSA is insured.

Figure 10:
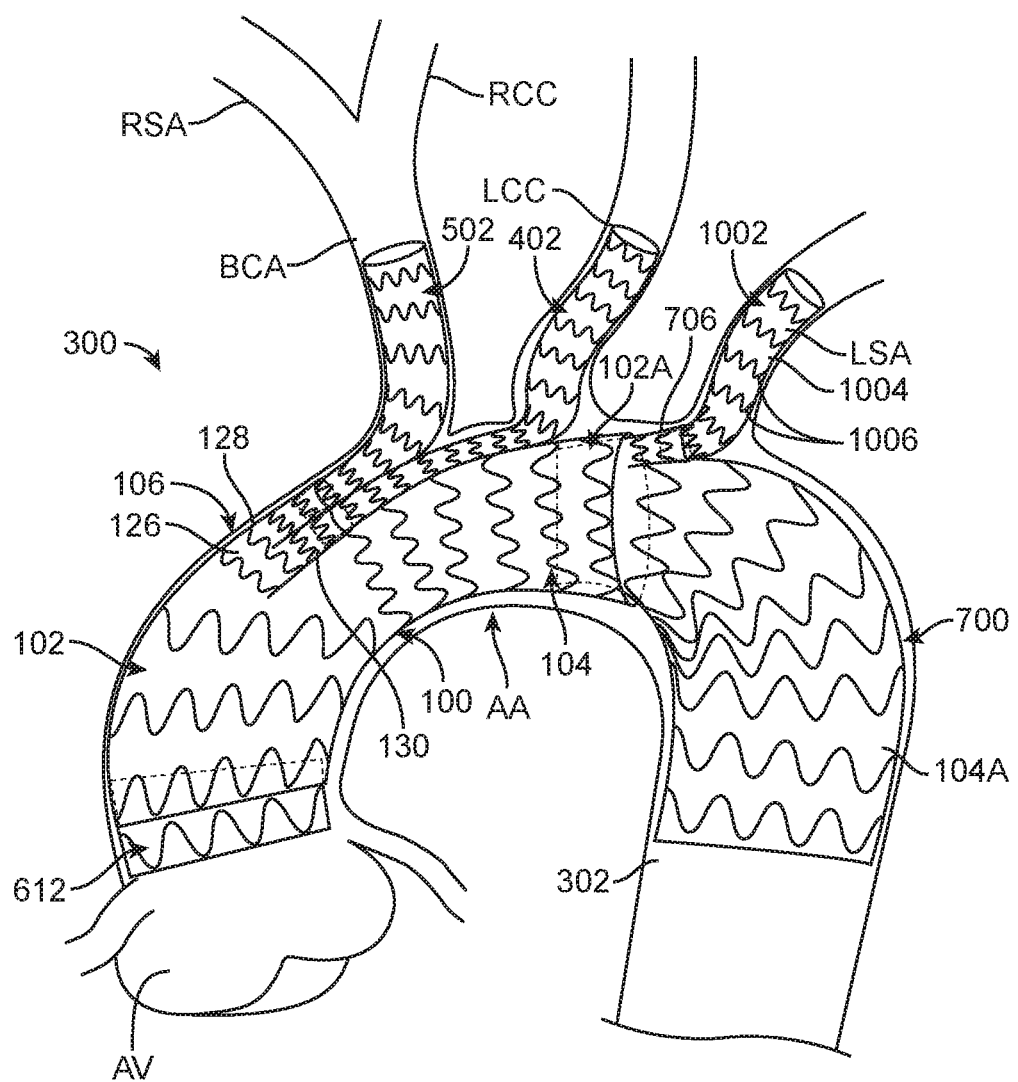
FIG. 10 is a cross-sectional view of the vessel assembly of FIG. 9 at a later stage during deployment of a bridging stent graft in accordance with one embodiment.

FIG. 10 is a cross-sectional view of vessel assembly 300 of FIG. 9 at a later stage during deployment of a bridging stent graft 1002, sometimes called a bridging stent, in accordance with one embodiment. Referring to FIGS. 9 and 10 together, bridging stent graft 1002 is deployed within artery branch 706 and the left subclavian artery LSA. More particularly, bridging stent graft 1002 self-expands (or is balloon expanded) to be anchored within artery branch 706 and the left subclavian artery LSA. Bridging stent graft 1002 is deployed via supra aortic access through the left subclavian artery LSA in a manner similar to that discussed above regarding deployment of bridging stent grafts 402, 502 or via femoral access.

Bridging stent graft 1002 includes graft material 1004 and one or more circumferential stents 1006. Upon deployment of bridging stent graft 1002, blood flow into artery branch 706 is bridged and passed into the left subclavian artery LSA through bridging stent graft 1002. In this manner, any overlapped diseased regions of the aorta 302 are excluded.

Although coupling of a distal component such as tube graft 602 in FIG. 6 and second modular stent device 700 in FIG. 10 to modular stent device 100 is described above and illustrated, in other embodiments, other distal components are coupled to modular stent device 100. For examples of other distal components, see Perkins et al., U.S. patent application Ser. No. 16/367,906, and issued as U.S. Pat. No. 11,116,650 on Sep. 14, 2021, entitled "SUPRA AORTIC ACCESS MODULAR STENT ASSEMBLY AND METHOD, filed Mar. 28, 2019, which is herein incorporated by reference in its entirety. Also see Perkins et al, U.S. patent application Ser. No. 16/367,889 and issued as U.S. Pat. No. 11,304,794 on Apr. 19, 2022, and Perkins et al., U.S. patent application Ser. No. 16/367,922, and issued as U.S. Pat. No. 11,083,605 on Aug. 10, 2021, cited above. Other distal extensions can be added using thoracic device to any of the embodiments as described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An assembly comprising:
an integral first modular stent device comprising:
 a main body configured to be deployed in an ascending aorta;
 a bypass gate configured to be deployed in an aorta; and
 a bifurcated contra limb, the main body being bifurcated into the bypass gate and the bifurcated contra limb, the bifurcated contra limb comprising:
  a proximal limb extending from the main body, the proximal limb comprising a single integral non-overlapping graft material;
  a first distal limb extending from the proximal limb; and
  a second distal limb extending from the proximal limb, wherein a graft material is sewn together at a septum to define the first distal limb and the second distal limb, the first distal limb being connected to the second distal limb at the septum, wherein the bifurcated contra limb is bifurcated from a single proximal opening to two distal openings, the two distal openings being aligned and coplanar,
wherein a distal end of the main body is directly sewn to the single integral non-overlapping graft material at a proximal end of the proximal limb and wherein proximal ends of the first distal limb and the second distal limb are directly sewn to the single integral non-overlapping graft material at a distal end of the proximal limb.

2. The assembly of claim 1 wherein the proximal limb is bifurcated into the first distal limb and the second distal limb.

3. The assembly of claim 2 wherein the bifurcated contra limb further comprises a transition region where the proximal limb is bifurcated into the first distal limb and the second distal limb.

4. The assembly of claim 3 wherein the proximal limb extends distally from a proximal end of the bifurcated contra limb to the transition region and comprises a single lumen.

5. The assembly of claim 4 wherein:
the first distal limb extends distally from the transition region to a distal end of the first distal limb and includes a single lumen.

6. The assembly of claim 5 wherein:
the second distal limb extends distally from the transition region to a distal end of the second distal limb and includes a single lumen.

7. The assembly of claim 1 wherein:
the proximal limb includes a longitudinal axis;
the first distal limb includes a longitudinal axis; and
the second distal limb includes a longitudinal axis, the longitudinal axes of the proximal limb, the first distal limb, and the second distal limb are parallel with one another when the first modular stent device is in a relaxed configuration.

8. The assembly of claim 1 wherein the second distal limb is radially inward of the first distal limb.

9. The assembly of claim 1 wherein the second distal limb is between the bypass gate and the first distal limb.

10. The assembly of claim 1 wherein the bifurcated contra limb has a greater radial force than a radial force of the bypass gate.

* * * * *